(12) United States Patent
Potiquet et al.

(10) Patent No.: US 6,339,327 B1
(45) Date of Patent: Jan. 15, 2002

(54) EDDY CURRENT PROBE FOR INSPECTING ELECTRICALLY CONDUCTING PARTS

(75) Inventors: Lyliane Potiquet, La Alle St Cloud; Hervé Schepens, Montigny le Bretonneux; Michel Pigeon, Bures en Fuelle, all of (FR)

(73) Assignee: Commissariat A l'Energie Atomique, Paris (FR)

( * ) Notice: Subject to any disclaimer, the term of this patent is extended or adjusted under 35 U.S.C. 154(b) by 0 days.

(21) Appl. No.: 09/341,293
(22) PCT Filed: Jan. 9, 1998
(86) PCT No.: PCT/FR98/00040
 § 371 Date: Aug. 2, 1999
 § 102(e) Date: Aug. 2, 1999
(87) PCT Pub. No.: WO98/30896
 PCT Pub. Date: Jul. 16, 1998

(30) Foreign Application Priority Data

Jan. 10, 1997 (FR) ............................................. 97 00203

(51) Int. Cl.[7] ............................................. G01N 27/72
(52) U.S. Cl. ........................ 324/220; 324/238; 324/239
(58) Field of Search ................................. 324/220, 232, 324/238, 225, 239, 240, 242, 243, 241

(56) References Cited

U.S. PATENT DOCUMENTS

| 4,789,827 A | * | 12/1988 | Bergander | 324/220 |
| 4,808,924 A | * | 2/1989 | Cecco et al. | 324/220 |
| 5,256,966 A | * | 10/1993 | Edwards | 324/220 |
| 5,506,503 A | * | 4/1996 | Cecco et al. | 324/220 |

* cited by examiner

Primary Examiner—Safet Metjahic
Assistant Examiner—Subhash A Zaveri
(74) Attorney, Agent, or Firm—Burns Doane Swecker & Mathis LLP

(57) ABSTRACT

The probe for inspecting electrically conducting parts (1) of the invention comprises a row of transmitter and receiver coils (27), (28) that form an array of energized coils. The receiver coils (28) are influenced by different magnetic fields created by several neighboring transmitter coils (27) at the same time, making them sensitive to different types of flaws. The array of energized coils is displaced along the row. The probes are usually used for inspecting steam generator tubes of nuclear power plants.

14 Claims, 6 Drawing Sheets

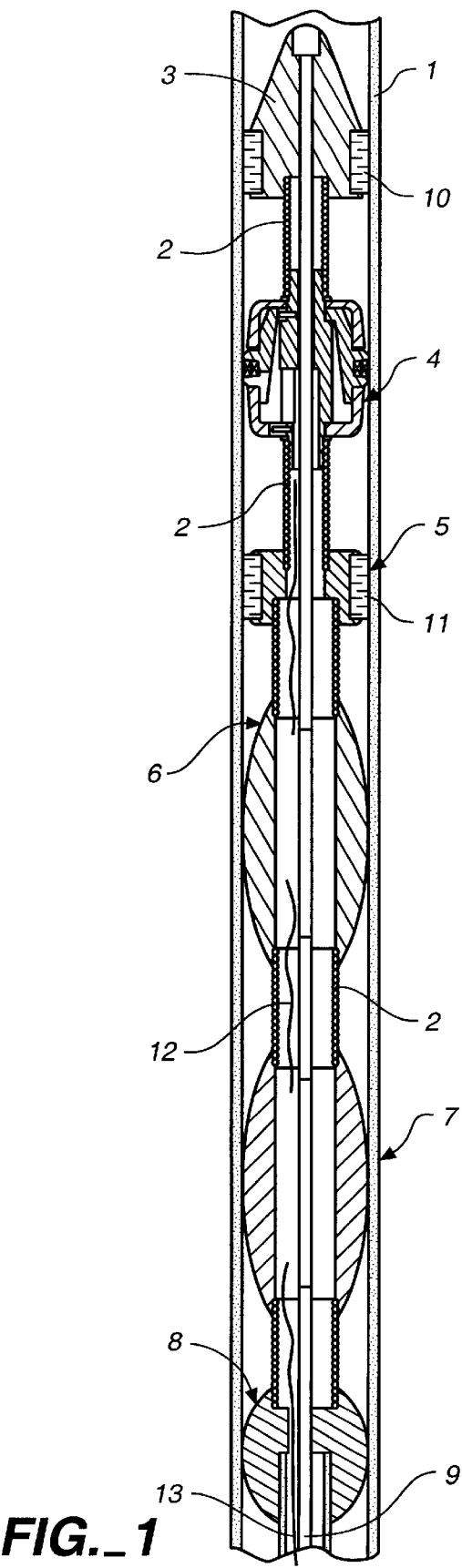
FIG._1

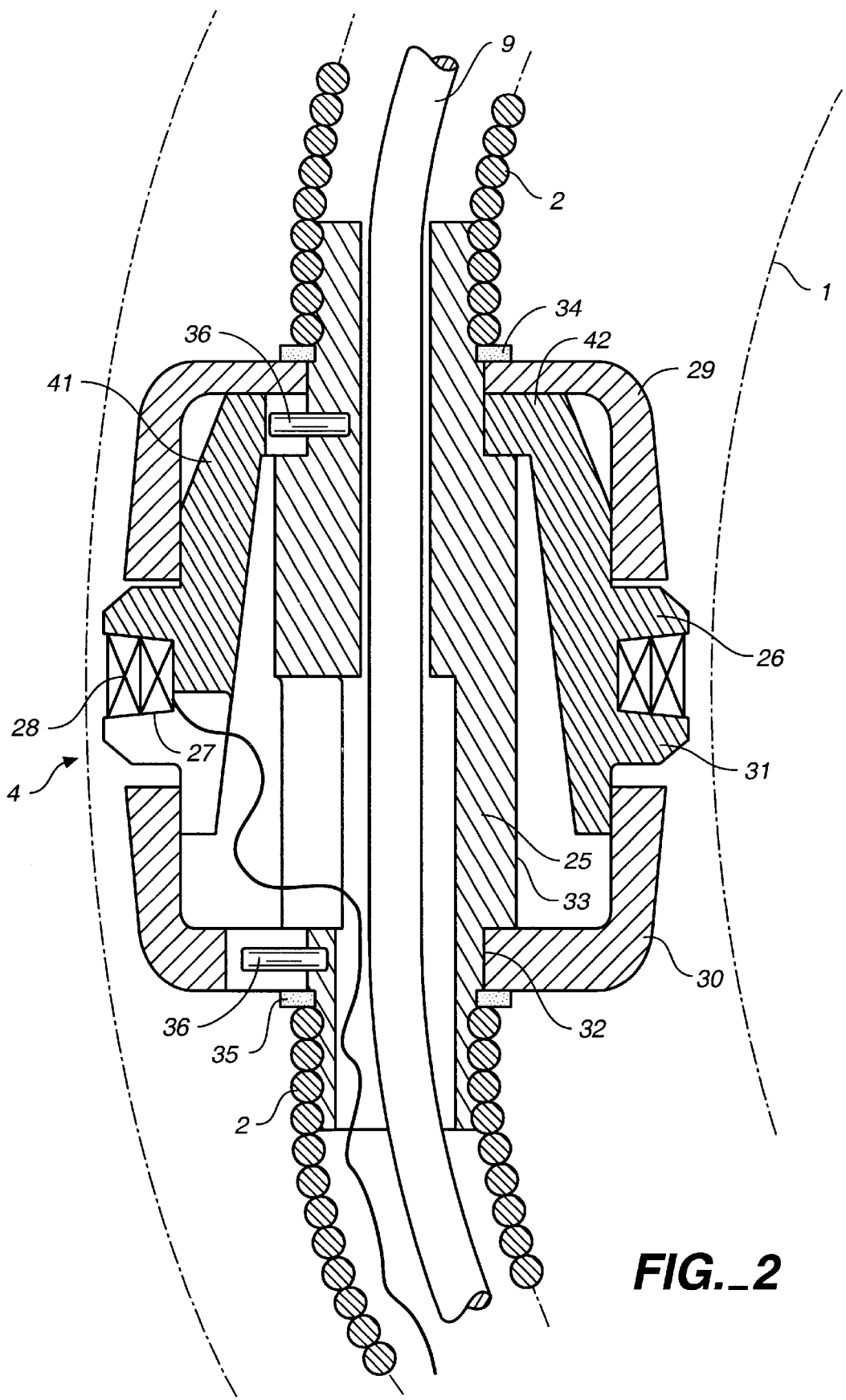
FIG._2

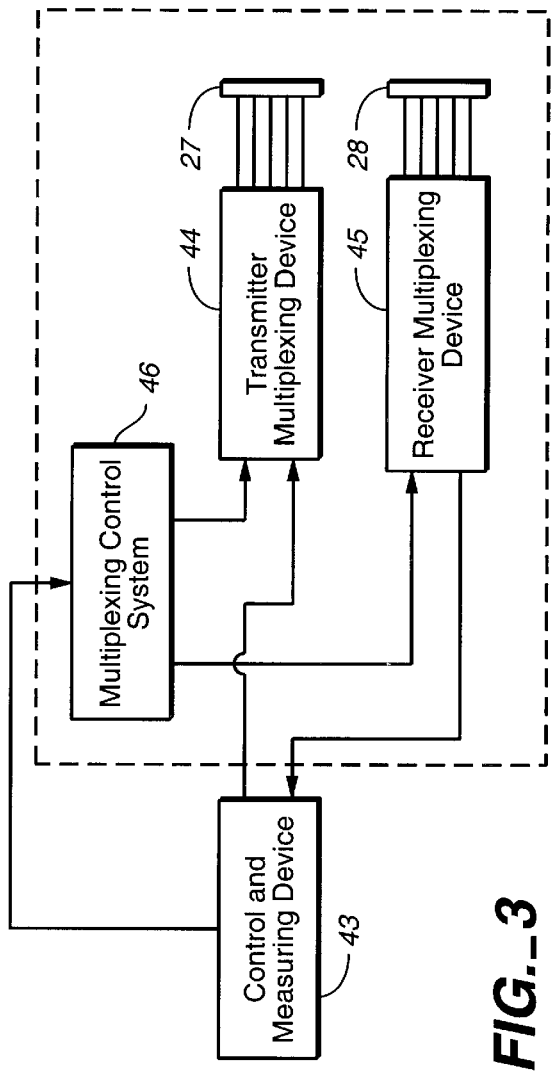
FIG._3
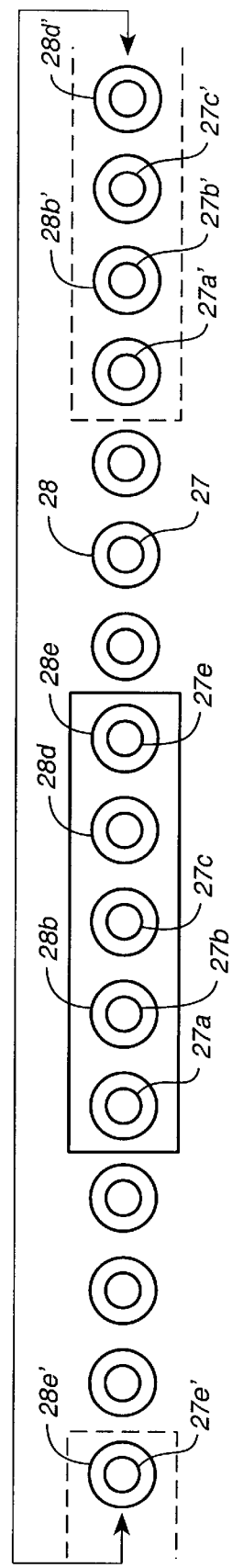
FIG._4

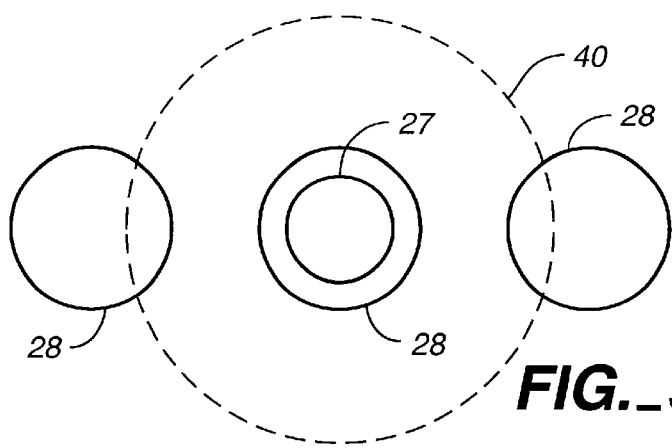
FIG._5
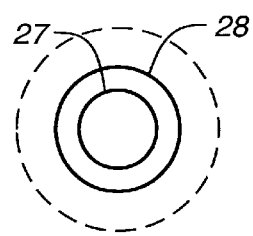
FIG._6A
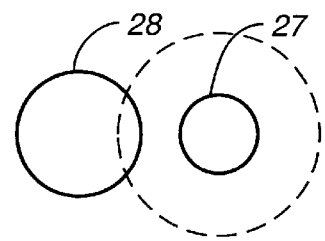
FIG._6B
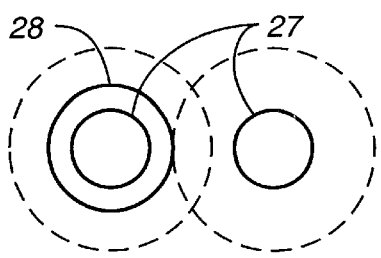
FIG._6C
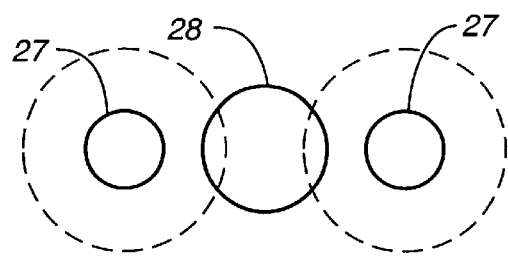
FIG._6D
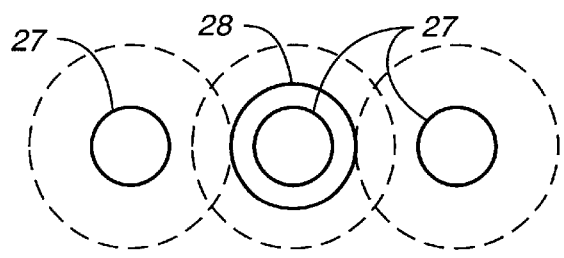
FIG._6E

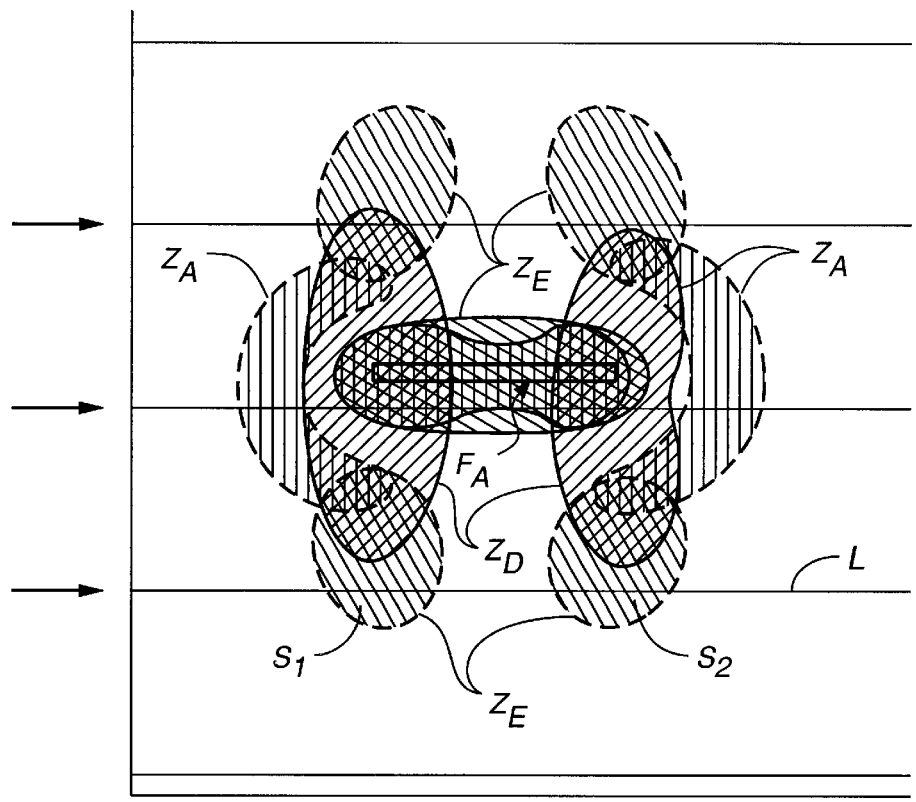
FIG._7A
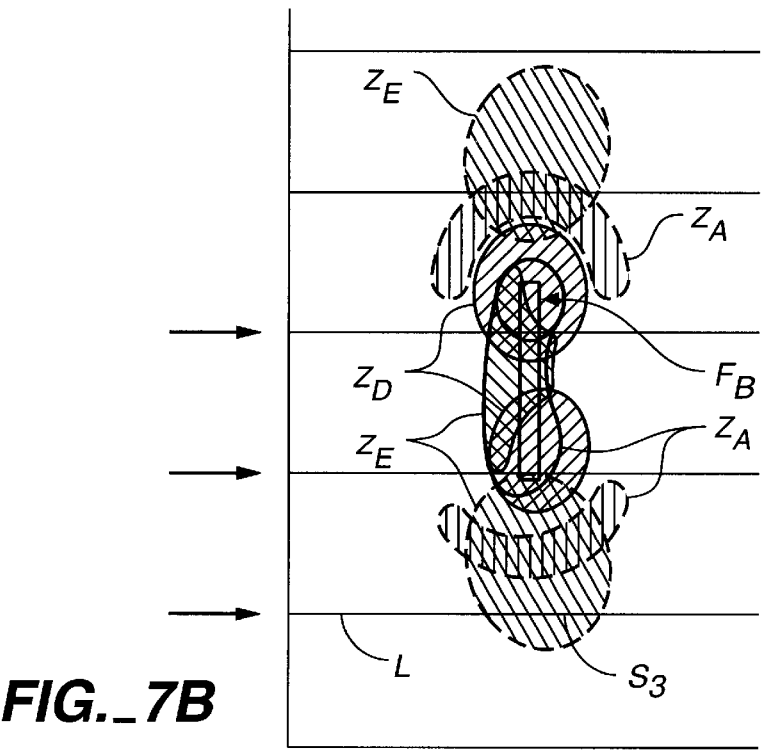
FIG._7B

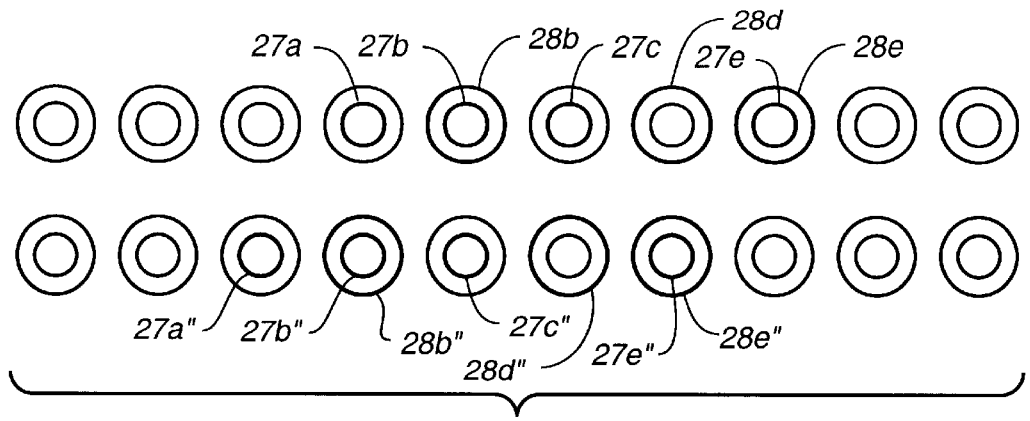
FIG._8
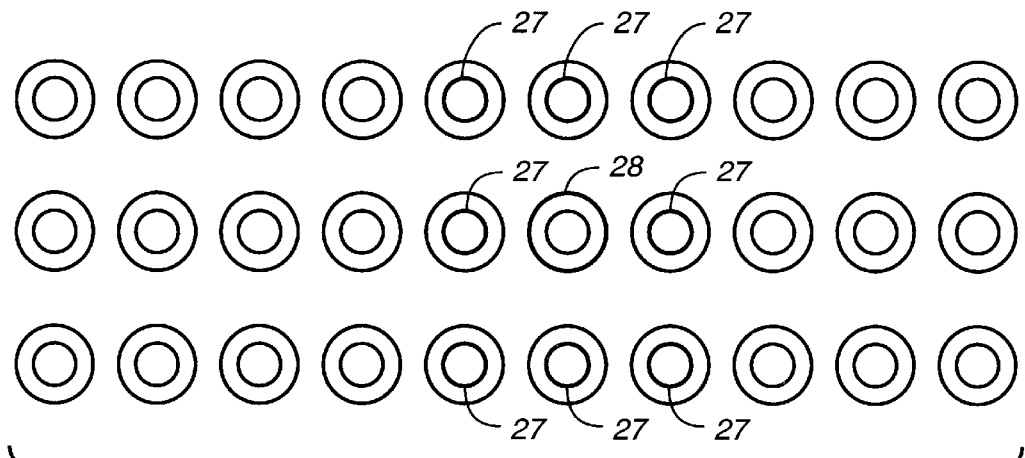
FIG._9
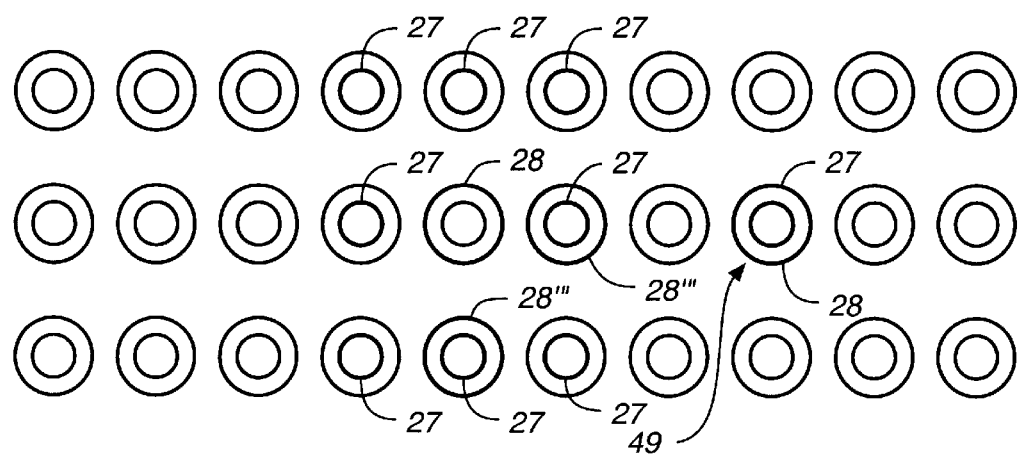
FIG._10

EDDY CURRENT PROBE FOR INSPECTING ELECTRICALLY CONDUCTING PARTS

FIELD OF THE INVENTION

The present invention relates to an eddy current probe that is particularly designed for inspecting the condition of conduits during maintenance of steam generators in nuclear power plants, said heat exchangers comprising a ring formed of a large number of elbow-shaped tubes in which the heat-exchanger fluid flows.

This type of inspection must be carried out rapidly, requiring the probes to move through the tubes at relatively high speeds of approximately 500 mm/s. The flow-sensitive sensors located at the tip of the probe must therefore be constructed and positioned to give sure, easy detection.

BACKGROUND ART

Several devices have been proposed in the prior art. For example, French patent 2,668,605 gives a detailed description of the chief components of a probe and mentions the possible use of ultrasound of eddy current sensors for carrying out the inspection without, however, giving much information on the best way of arranging the sensors. In contrast, U.S. Pat. No. 5,256,966 describes a probe that only uses eddy currents. Eddy current sensors are fitted with sensing coils through which an AC current is passed, creating a magnetic field around the coils, and receiver coils connected to a circuit of which the impedance is measured. This impedance is governed by the eddy currents produced by the magnetic field in the neighboring conducting material, i.e. inside the material constituting the tube, and the impedance varies when flaws in the tube cause local increases in resistance and modify the way the eddy currents flow. The flaws in the tube are thus identified by variations in impedance on the terminals of the receiver windings.

The coils of U.S. Pat. No. 5,256,966 are both transmitters and receivers and are either positioned on a single ring or, where space is an issue, placed alternately on two neighboring rings. This is done with the aim of transmitting a magnetic field over the entire circumference of the tube in order to detect flaws which would go undetected if there were spaces between the magnetic fields created by individual coils. This arrangement, in which a plurality of sensors is used, is made possible using a switching device that makes it possible simultaneously to activate only some of the sensors, together with a multiplexing device which is used to transmit by turns data from one series of sensors along each measuring wire.

A different design is described in an article by Sullivan et al. entitled "Detection coverage of transmit-receive eddy currents array probes" that was distributed during the 14th EPRI Steam Generator NDE Workshop held in Seattle between Aug. 7 and 9, 1995. This system uses four magnetic field-emitting coils placed around the circumference of the probe together with two rows of four receivers each of which is positioned on either side of the row of transmitters and surrounding the transmitter coils. In this design the transmitters and receivers are thus separate coils and each transmitter is surrounded by four receivers that are sensitive to the eddy currents it induces. Measurements are differential, meaning that the result produced on the receivers of one row is subtracted from the result of the respective receivers of the other row.

Known probes all have drawbacks as concerns the detection of flaws. The probe described in the Sullivan article is effective in detecting transversal cracks, particularly the ends of such cracks, but is insensitive to longitudinal flaws. The probe described in the US patent has the drawback of being insensitive to certain flaws, particularly longitudinal flaws located mid-way between neighboring coils where the fields produced by adjacent coils balance one another out. More surprisingly, it is also insensitive to flaws whose edges lie mid-way between adjacent coils. U.S. Pat. No. 5,506,503 describes how, within a probe having a row of alternately transmitting and receiving coils, certain transmitter coils may be disactivated one by one to detect additional flaws. This statement would suggest a need to scan the part being inspected several times with different transmitter coils activated during each scan, which is clumsy and time-wasting.

The aim of the present invention is both to detect all the flaws, particularly cracks, in the surface being inspected, irrespective of their orientation. The preferred embodiments of the invention are satisfactorily sensitive to all types of flaw and the part to be inspected is always covered in a single scan.

The invention is based on using an array of simultaneously active transmitting and receiving coils that does not vary in shape and that is moved across the width of the part being inspected, either by moving the probe (transversal and particularly using a rotating movement for a circular probe) or by switching the coils. The receiver coils in the array are subjected to different magnetic fields and are thus sensitive to different flaws in the part being inspected.

The invention relates to a probe for inspecting a conducting part characterized in that it comprises:
  a body fitted with at least one row of identical pairs of adjacent transmitting and receiving coils;
  means for activating the transmitting coils by energizing them by means of an AC current of sufficient amplitude to create a magnetic field that extends as far as the receiver coils of the neighboring pairs in the row to those belonging to the energized transmitter coils;
  means for activating the receiver coils while measuring signals induced in them by the magnetic field;
  and means for displacing a coil array composed of energized transmitter and receiver coils in the direction of the row, said array comprising at least two transmitter coils and one receiver coil, the coils of the array remaining in the same relative positions.

The invention will now be described with reference to the following Figures, which are attached as non-limitative examples. The Figures disclose certain preferred embodiments of the invention together with their advantages:

FIG. 1 shows a tube inspecting probe;
FIG. 2 shows a measuring module or a probe body fitted with sensors;
FIG. 3 shows the means for controlling the probe;
FIG. 4 shows the row of sensors;
FIG. 5 shows the range of a magnetic field created by a transmitter coil;
FIGS. 6A, 6B, 6C, 6D and 6E show various possible situations for a receiver coil;
FIGS. 7A and 7B show the detection range of a receiver coil with two different types of flaw;
FIGS. 8, 9 and 10 show three advantageous arrays of energized transmitting and receiver coils.

In FIG. 1 the probe of the invention is shown housed in tube 1. The probe consists of a series of components connected to one another by linking springs 2. Working from the front of the probe backwards, there is first a nose-piece 3, a measuring module 4 that bears the sensors, a guiding component 5, a connection carriage 6, an electronics carriage 7 and a connecting component 8. A cable 9 passes through the preceding components, making it possible to recover them if the probe breaks. Said cable is crimped into nose-piece 3. Nose-piece 3 is bullet-shaped and tapers towards the front while carriages 6 and 7 and connecting component 8 are oval with a central portion of a diameter almost equal to the inner diameter of tube 1 which can therefore guide them. In addition, centering brushes 10 and 11 are provided forward of and behind measuring module 4, on nose-piece 3 and guiding component 5 to rub against tube 1, thereby ensuring accurate centering of measuring module 4. Connection and electronics carriages 6 and 7 contain housing cavities for equipment and electrical cables 12 that connect the outside to measuring module 4. Springs 2 protect cables 12 between the series of components and a sheath 13 similarly protects them behind connecting component 8. The main purpose of sheath 13 is to force the components of the probe along tube 1.

FIG. 2 shows that the measuring module 4 includes a support bush 25 through which cable 9 passes, a ring 26 that is placed around support bush 25 and carries transmitter and receiver coils 27 and 28, and a casing formed from two halves 29 and 30 that enclose and retain ring 26 while creating a gap through which a circular protuberance 31 passes, bearing coils 27 and 28 of ring 26. More precisely, ring 26 and casing halves 29 and 30 are centered on a cylindrical surface 32 of support bush 25 and maintained in translation against a shoulder 33 of support bush 25 provided in the middle of cylindrical surface 32. Elastic seals 34 and 35 retain ring 26 and casing halves 29 and 30 against said shoulder 33. The front and rear of cylindrical surface 32 are fitted with helicoidal grooves that house springs 2. Similar arrangements are provided for the other components in the series to retain springs 2. Hasps 36 retain at least ring 26 rotating around support bush 25 to maintain its angular position during examination of tube 1. Since circular protuberance 31 is assumed to rub against the inner surface of 1, it can do this when slight displacements occur or when tube 1 is distorted. This is why ring 26 is made flexible so that circular protuberance 31 may be inserted between casing halves 29 and 30. Circular protuberance 31 may be split to separate lugs 41, each of which carries a transmitter and a receiver coil 27 and 28 respectively, and lies between these coils and a conical connection portion 42 that lies adjacent to bush 29.

The system comprises sixteen transmitter coils 27 and the same number of receiver coils 28 of which two of each type are shown facing one another. A receiver coil 28 is superimposed on each transmitter coil 27 and coaxial with it. It is, however, possible for transmitter and receiver coils of each pair to be placed adjacent to one another, in particular in two parallel rows. FIG. 3 is a block diagram of the detector control system. It comprises an external control and measuring device 43 that transmits an excitation signal and receives signals from the energized receiving coils 28. In order to do this it is connected to a transmitter multiplexing device 44 and a receiver multiplexing device 45 that are connected respectively to all the transmitter and receiver coils 27, 28 and located in the connection carriage 4 and which continuously select the energized coils. In order to switch the coils, the control and measuring device 43 is again connected to a multiplexing control system 46 and sends it a periodic switching signal that the multiplexing control system 46 transmits to multiplexing devices 44 and 45 to change the energized coils. The multiplexing control system is located in the electronics carriage 7. The multiplexing procedure adopted here, which only uses some of the coils at a time, makes it possible to reduce the number of wires connecting the probe to the outside. In practice, the energized coils are very rapidly switched in order to scan the inside of tube 1 at a speed many times greater, for example 120 times, than the speed of travel of the probe.

It is a feature of the invention that transmitter and receiver coils 27 and 28 that are simultaneously energized form an array that is usually irregular in shape and that is displaced on the circumference of tube 1 to detect the flaws of every type it contains. The general principle is that the receiver coils 28 of the array must be subject to different magnetic fields to be more sensitive to different flaws. This is achieved if the transmitter coils 27 affecting them are at different locations each time. Several suitable arrays may be designed using this principle depending on the range of the magnetic fields and the positioning of the coils. We here suggest the measuring device shown in FIG. 4: the ring of sixteen pairs of transmitter and receiver coils 27 and 28 is shown flat and coils that are simultaneously energized belong to five consecutive pairs noted successively a, b, c, d and e. The transmitter coils 27 of these pairs are all active except the fourth and the receiver coils 28 of the second, fourth and fifth pairs are also energized. In other words, coils 27a, 27b, 28b, 27c, 28d, 27e and 28e are simultaneously energized and this group of energized coils moves in either direction along the ring of sensors 27 and 28 depending on the switching.

The reason why this configuration has been chosen will be explained with reference to the following figures. FIG. 5 shows that the transmitter coils 27 are chosen so that their magnetic field extends as far as the two receiver coils 28 of the adjacent pairs, i.e. the two adjacent receiver coils 28 are sensitive to the eddy currents created by the transmitter coil 27. This transmitter coil 27 influences receiver coil 28, with which it forms a pair, even more strongly. When a flaw in tube 1 is present in magnetic field 40, the eddy currents induced by this field are modified; this modification is measured by the three influenced receiver coils 28. It will, however, be noted that the shape, position and orientation of the flaw have a significant effect on modifying currents such that certain flaws may go almost undetected.

The inventors have found that different relative positions of a transmitter coil 27 and a receiver coil 28 assisted in the detection of various flaws. For the rest of the present argument, it is easiest to use receiver coil 28 as the reference point: FIGS. 6A, 6B and 6C show that there are three elementary possible ways a receiver coil 28 may be sensitized: by the magnetic field 40 of a transmitter coil 27 of the same pair, of the neighboring pair, or both at the same time. FIGS. 6D and 6E are symmetrical versions of FIGS. 6B and 6C and show that the same receiver coil 28 may be sensitized by transmitter coils 27 of the two neighboring pairs and possibly also by the transmitter coil 27 of the same pair.

Returning to FIG. 4, it will be seen that while coil 28b is in the situation shown in FIG. 6E, coil 28d is in the situation shown in FIG. 6D and coil 28e is in the situation shown in FIG. 6A. The greatest possible sensitivity to all types of flaw is thus ensured for this sensor configuration.

FIGS. 7A and 7B show results obtained using the three coil configurations of FIGS. 6A, 6D and 6E. These figures show areas of flaw sensitivity: the horizontal axis of the abscissas represents the axis of tube 1, i.e. the direction in which the probe moves. The vertical ordinate axis is the direction of the ring of coils 27 and 28 or the direction of the circumference of tube 1. It is assumed that three pairs of coils move along the arrows defining the lines of detection. The areas of sensitivity of a central receiver coil 28 sensitized by one, two or three transmitter coils 27 placed as shown in FIGS. 6A, 6D and 6E respectively are referred to as ZA, ZB and ZE. The flaws shown are a longitudinal crack FA in FIG. 7A and a transversal crack in FIG. 7B. Practically speaking, when these lines of detection pass through areas of sensitivity the receiver coil 28 is sensitive to the existence of the flaw. If, for example, longitudinal crack FA is considered, the horizontal L is plotted using the position of the coils and the intersections of this line L with regions Z are examined. The horizontal lines represent the axes of the coils and may be located in any position relative to the crack. In the example shown, two segments S1 and S2 lie within two portions of the region ZE, showing that the flaw will be detected using the arrangement of FIG. 6E along the lengths of trajectory S1 and S2 of the probe. A similar argument holds good for FIG. 7B in which the horizontal line L passes through regions of sensitivity of transversal crack FB. Segment S3 is the length of the trajectory of the probe for which the transmitter coil 27 as configured in FIG. 6E detects crack FB.

The essential point to be drawn from these figures is that the simultaneous presence of the three coil configurations greatly increases the detection performance sensitivity of the probe. In particular, FIG. 7A shows that the areas of detection of longitudinal cracks are wide both in the transversal and axial directions, thereby considerably reducing the risk of the probe passing over crack F too rapidly to detect it. FIG. 7B shows that the total detection area is continuous in the transversal direction so that transversal cracks do not escape detection either. Since coils 27 and 28 are rapidly switched relative to the progress of the probe, areas ZA, ZD and ZE are correctly positioned in the locations given for the three pairs of coils shown.

However, the arrangement given above is not essential and other coil configurations are possible.

FIG. 4 shows an example in which two groups of coils identical to the above description and positioned along the row—transmitter coils 27a, 27b, 27c and 27e and receiver coils 28b, 28d and 28e, on the one hand, and transmitter coils 27a', 27b', 27c' and 27e' and receiver coils 28b', 28d' and 28e', on the other hand—may operate simultaneously. It is possible to have more than two identical or different groups operating simultaneously to increase the quantity of data.

A few other possible embodiments will now be described. The embodiment shown in FIG. 8 comprises two parallel rows of transmitter and receiver coils 27 and 28. The array of energized coils for the first five pairs alone (i.e. 27a to 27e and 28a to 28e) in the second row reproduces that shown in FIG. 4. The array of each row is thus composed of the first, second, third and fifth transmitter coils 27a, 27b, 27c and 27e or 28a", 27b", 27c" and 27e" respectively and the second, fourth and fifth receiver coils 28b, 28d and 28e or 28b", 28d" and 28e" respectively. The energized coils are also offset by one pair of coils between the two rows, i.e. the first, second, third and fourth pairs of the first row face the second, third fourth and fifth pairs of the second row and the coils of the last two pairs of the array (27a", 27e and 28e) are facing inactive coils. Furthermore, their matching receiver coils (28b and 28b", 28d and 28d", and 28e and 28e") are coupled by the control and measuring device 43 which makes subtractions from their measurements. This differential measurement procedure improves the detection of flaws, particularly of transversal flaws, in tube 1.

FIG. 9 shows another advantageous array in which the superimposed pairs of transmitter and receiver coils 27 and 28 are arranged in three parallel rows. This array comprises a single receiver coil 28 in the middle row but eight transmitter coils 27, two of which are placed on the middle row adjacent to the receiver coil 28 and three on each of the two outer rows, facing coils 27 and 28 of the array on the middle row so that the transmitter coils 27 of the array are at the corners and in the middle of the sides of a rectangle (a square in the figure) of which the receiver coil 28 occupies the center. This array has greater depth of penetration than the previous embodiments i.e. it is better at detecting deeper flaws.

Lastly, FIG. 10 shows that it is possible to combine the arrays of FIGS. 4 and 9 into a single array; to the array of FIG. 9 is added a pair 49 of transmitter and receiver coils 27 and 28 that are superimposed and insulated from the main array, for example a pair of coils, to prevent them being influenced by its field. This enables them to operate like the array of FIG. 6A; one or two receiver coils 28'" are added in the middle of as many sides of the rectangle in order to reproduce the array of FIG. 6E.

The invention is not limited to circular probes for examining tubes; it may be applied, for example, to inspecting flat metal sheets. For this purpose the coils are fitted onto a straight mounting.

Another possibility is not to use the switching/multiplexing apparatus and to fit the coils onto a rotating or, more generally speaking, transversally mobile measuring module as has already been proposed. This solution makes it possible greatly to reduce the number of coils since while the energized coils remain the same and the others are disactivated, this requires a more complicated probe due to the need to add a motor and electrical and mechanical couplings between the fixed and rotating components of the probe. This is why the probe shown in the figures is more advantageous.

Each transmitter coil 27 is powered simultaneously or alternately at a single frequency or at multiple frequencies in order to modify the inspection depth using the principle disclosed in French patent 2,324,003. It is also possible to use combinations of signals to eliminate interference, for example due to signals from insert plates in steam generators.

What is claimed is:

1. Probe for inspecting electrically conducting parts, comprising:
   a body (4) fitted with at least one row of identical pairs of adjacent transmitting (27) and receiving (28) coils;
   a means for activating three successive ones of the transmitting coils by energizing them via an AC current of sufficient amplitude to create respective magnetic fields;
   a means for activating one of the receiver coils while measuring signals induced therein, said one of the receiver coils being coaxial to a central one of said three transmitting coils;
   said three of the transmitting coils and one of the receiver coils composing an active coil array;
   said one of the receiver coils being sensitive to all said respective magnetic fields; and
   a means for displacing said coil array along the row.

2. Probe of claim 1, said receiver coil of the array is located between the transmitter coils of the array, the coils of the array belonging to three neighboring pairs of the row.

3. Probe of claim 2, said array including the transmitter coil of the receiver coil of the array.

4. Probe of claim 1, said array comprises five successive pairs of coils, more precisely the transmitter coils (27a, 27b, 27c and 27e) of the first, second, third and fifth pairs and the receiver coils (28b, 28d and 28e) of the second, fourth and fifth pairs of the five successive coils.

5. Probe of claim 1, said probe further comprising two parallel rows of pairs of coils and the array comprises, on the first row, five successive pairs of coils, and on the second row five successive pairs of coils, the pairs of the array being offset by one pair of coils between the first and second rows.

6. Probe of claim 1, said probe further comprising three parallel rows of pairs of coils and the array comprises, in two of the rows, three transmitter coils and, on a third row, two transmitter coils and one receiver coil, the transmitter coils being located at the corners and in the middle of the side of a rectangle of which the receiver coil occupies the center.

7. Probe of claim 6, said array comprises an additional receiver coil located in the middle of one side of the rectangle and a receiver coil and a transmitter coil of the same pair of coils located outside the magnetic field produced by the transmitter coils of the rectangle.

8. Probe of claim 1, said transmitter and receiver coils of each pair are superimposed and coaxial.

9. Probe of claim 1, said means for activating three successive ones of the transmitting coils comprise a switching means.

10. Probe of claim 9, said row extends across the entire width of the body and the array is displaced within the row by switching the coils of the array.

11. Probe of claim 1, said body can move laterally and the array extends across all the coil pairs.

12. Probe of claim 1, said probe further comprising a plurality of coil patterns active simultaneously, wherein the respective coil patterns provide the selective detection of different flaws.

13. Probe of claim 12, said plurality includes at least three active receiver (28) coils.

14. Probe of claim 13, wherein said plurality further includes at least four active transmitting (27) coils.

* * * * *